(12) United States Patent
Miyagi et al.

(10) Patent No.: US 6,281,224 B1
(45) Date of Patent: *Aug. 28, 2001

(54) PRANOPROFEN EYEDROPS CONTAINING ORGANIC AMINE

(75) Inventors: Shogo Miyagi, Kobe; Yoshihide Horibe, Higashiosaka, both of (JP)

(73) Assignee: Santen Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/945,198

(22) PCT Filed: Apr. 16, 1996

(86) PCT No.: PCT/JP96/01035

§ 371 Date: Oct. 20, 1997

§ 102(e) Date: Oct. 20, 1997

(87) PCT Pub. No.: WO96/32941

PCT Pub. Date: Oct. 24, 1996

(30) Foreign Application Priority Data

Apr. 20, 1995 (JP) .................................................. 7-094723

(51) Int. Cl.$^7$ .................................................. A61K 31/44
(52) U.S. Cl. ........................................... 514/291; 514/912
(58) Field of Search ..................................... 514/291, 912

(56) References Cited

U.S. PATENT DOCUMENTS

| 4,725,586 | * | 2/1988 | Lindstrom et al. ................. 514/54 |
| 4,829,083 | | 5/1989 | Doulakas . |
| 4,829,088 | | 5/1989 | Doulakas . |
| 5,414,011 | | 5/1995 | Fu et al. . |

FOREIGN PATENT DOCUMENTS

| 59-89616 | 5/1984 | (JP) . |
| 61-12617 | 1/1986 | (JP) . |
| 62-242617 | 10/1987 | (JP) . |
| 62-242618 | 10/1987 | (JP) . |
| 1-29170 | 6/1989 | (JP) . |
| 2-286627 | 11/1990 | (JP) . |
| 5-186349 | 7/1993 | (JP) . |
| 7-17863 | 1/1995 | (JP) . |
| 60-184013 | 9/1995 | (JP) . |
| WO 87/00753 | 2/1987 | (WO) . |

* cited by examiner

Primary Examiner—Zohreh Fay
(74) Attorney, Agent, or Firm—Frishauf, Holtz, Goodman, Langer & Chick, P.C.

(57) ABSTRACT

An ophthalmic solution containing 0.01 to 0.5 weight % of pranoprofen and 0.1 to 5.0 weight % of an organic amine, such as tromethamine or 4-(2-hydroxyethyl)-1-(2-sulfoethyl)piperazine. Such solution has a desirable stability and does not cause undue irritation when administered to eyes to treat an inflammatory disease such as keratoconjunctivitis.

19 Claims, No Drawings

PRANOPROFEN EYEDROPS CONTAINING ORGANIC AMINE

TECHNICAL FIELD

The present invention relates to a pranoprofen ophthalmic solution containing an organic amine, and the ophthalmic solution is characterized in that a change in the composition thereof does not occur, the stability is excellent and irritation is little.

BACKGROUND TECHNIQUES

Pranoprofen is an acidic non-steroidal anti-inflammatory drug which is a propionic acid derivative, is useful for inflammatory diseases in the ophthalmic field such as keratoconjunctivitis in an extraocular area and an anterior segment of the eye, and has been put into practice in the form of an ophthalmic soluton. Pranoprofen can stimulate the eyes and, therefore, a variety of attempts have been made to suppress the irritation in order to prepare ophthalmic solutions. For example, there have been proposed a method by addition of boric acid (Japanese Laid-open Patent Publication No. 60-184013), a method by addition of carbonate (Japanese Laid-open Patent Publication No. 5-186349) and a method by addition of acetate ion (Japanese Laid-open Patent Publication No. 7-17863) to reduce such irritation.

On the other hand, an attempt at preparing ophthalmic solutions and intraocular Irrigating solutions containing an organic amine have been also made. For example, in a case of an ophthalmic solution containing sulfa drugs, there has been disclosed a method for making it possible to solubilize sulfa drugs and enhancing the preservative properties by addition of an alkanolamine such as monoethanolamine, diethanolamine or triethanolamine in ophthalmic solutions containing a sulfa drug and, thereby, (Japanese Patent Publication No. 1-29170, Japanese Laid-open Patent Publication No. 59-89616 and Japanese Laid-open Patent Publication No. 61-12617). In addition, there have been also disclosed diclofenac sodium ophthalmic solutions containing tromethamine or a homologue thereof having 10 or less carbon atoms as preservatives and a stabilizing agent (Japanese Laid-open Patent Publication No. 62-242617, Japanese Laid-open Patent Publication No. 62-242618), and intraocular irrigating solutions containing chondroitin sulfate in which 4-(2-hydroxyethyl)-1-(2-sulfoethyl)piperazine (hereinafter referred to as "HEPES") is formulated (PCT WO87/00753 and U.S. Pat. No. 4725586).

However, there has not been reported yet preparations of ophthalmic solutions containing pranoprofen as an active ingredient and in which an organic amine is formulated.

It is an interesting theme to find ophthalmic solutions containing pranoprofen as an active ingredient, which has an excellent stability and little irritation to eyes.

An object of the present invention is to provide ophthalmic solutions containing pranoprofen as an active ingredient, which has no change in the composition, an excellent stability and little irritation to eyes.

In order to find pranoprofen ophthalmic solutions having an excellent stability and little irritation to eyes, the present inventors studied extensively. As a result, the present inventors found that ophthalmic solutions which have no change in the composition, an excellent stability and little Irritation to eyes can be prepared by addition of an organic amine such as tromethamine or HEPES.

SUMMARY OF THE INVENTION

The present invention relates to an ophthalmic solution containing pranoprofen as an active ingredient, in which an organic amine is formulated (hereinafter referred to as "the present ophthalmic solution").

Preferred organic amines used in the present ophthalmic solution is alkanolamines such as tromethamine, monoethanolamine, diethanolamine and triethanolamine; sulfoalkyl piperazines such as HEPES, 1,4-bis(2-sulfoethyl)piperazine (hereinafter referred to as "PIPES"), 1,4-bis(3-sulfopropyl)piperazine (hereinafter referred to as "PIPPS") and 1,4-bis(4-sulfobutyl)piperazine (hereinafter referred to as "PIPBS"); sulfoalkyl alkylenediamines such as N,N'-bis(3-sulfopropyl)ethylenediamine (hereinafter referred to as "EDPS"). Tromethamine and HEPES are particularly preferable.

The concentration of the organic amine to be used can be appropriately selected and, in a case of tromethamine and HEPES, 0.1 to 5.0%, inter alia, 0.5 to 2.5%, particularly 2.0% is preferable.

The concentration of pranoprofen which is an active ingredient in the present ophthalmic solution to be used can be appropriately selected depending upon symptoms and 0.01 to 0.5%, particularly 0.1% is preferable.

Additionally, preseratives are formulated in the present ophthalmic solution, if necessary. Presertives widely used in the ophthalmic solutions can be used and, in particular, benzalkonium chloride is preferable and the concentration thereof to be used is preferably 0.002 to 0.01%, more preferably 0.005%.

The pH of the present ophthalmic solution can be in a range which is acceptable to ophthalmic preparations, and a range of 6.5 to 8.5 is preferable and a range of 7.6 to 8.0 is particularly preferable in viewpoint of the eye irritating properties.

As used herein, the concentration of each ingredient in the present invention is expressed as % by weight (w/v).

Pranoprofen is useful for inflammatory diseases in the ophthalmic field such as keratoconjunctivitis in an extraocular area and an anterior segment of the eye, and has been put into practice in the form of an ophthalmic solution. Pranoprofen causes ocular pain because of irritation to eyes. In order to suppress the irritation, a variety of attempts have been made (Japanese Laid-open Patent Publication No. 60-184013, Japanese Laid-open Patent Publication No. 5-186349, Japanese Laid-open Patent Publication No. 7-17863). Further, there is a demand for development of ophthalmic solutions having reduce irritating properties.

On the other hand, there have been disclosed sulfa drug-containing ophthalmic solutions which contain an organic amine (Japanese Patent Publication No. 1-29170, Japanese Laid-open Patent Publication No. 59-89616, Japanese Laid-open Patent Publication No. 61-12617), diclofenac sodium ophthalmic solutions (Japanese Laid-open Patent Publication No. 62-242617, Japanese Laid-open Patent Publication No. 62-242618) and intraocular irrigating solution containing chondroitin sulfate (PCT WO87/00753, U.S. Pat. No. 4,725,586). However, heretofore there has been no report on pranoprofen ophthalmic solutions containing an organic amine.

Then, in order to find pranoprofen ophthalmic solutions having an excellent stability and little irritation to eyes, the present inventors extensively studied preparations containing an organic amine.

As a result, as detailed data will be shown in the Examples hereinbelow and the section entitled "Effect of the invention", it was found that the present ophthalmic solution has no change in the composition, a high pranoprofen remaining rate, no pH change, and reduced eye irritation properties and, thus, is useful as an ophthalmic solution having pranoprofen as an active ingredient.

A general process for preparation of the present ophthalmic solution is as follows: An organic amine is added to sterile purified water, and pranoprofen is added thereto while stirring to completely dissolve it. To this is added a preserative to dissolve it, the pH is adjusted with hydrochloric acid or sodium hydroxide, and the solution is finally sterilized by filtration to obtain the present ophthalmic solution.

In addition, isotonic agents such as sodium chloride and concentrated glycerin, non-ionic surfactants such as polyoxyethylene sorbitan monooleate (hereinafter referred to as "polysorbate 80"), stearic polyoxyl 40 and polyoxyethylene hydrogenated castor oil, stabilizing agents such as sodium edetate and sodium citrate can be added thereto together with the organic amine, as necessary.

The following examples for formulating the preparations of the present ophthalmic solution are for better understanding of the present invention but do not limit the scope thereof.

BEST MODE FOR CARRYING OUT THE INVENTION

Preparation Example
Reference Example

Boric acid (1.6 g), sodium borate (0.8 g), polysorbate 80 (0.1 g) and sodium edetate (0.01 g) were added to sterile purified water (80 ml), and pranoprofen (100 mg) was added thereto while stirring to completely dissolve it To this was added benzalkonium chloride (5 mg) to dissolve it, an appropriate amount of hydrochloric acid or sodium hydroxide was added thereto to adjust the pH to 7.6, sterile purified water was added thereto to a total volume of 100 ml. The resulting colorless and clear solution was finally sterilized by filtration to obtain a 0.1% pranoprofen ophthalmic solution as reference preparation 1.

Then, reference preparations 2 to 5 were prepared according to the similar manner as that described above by fixing the concentration of pranoprofen at 0.1% and setting the concentrations of boric acid, sodium borate, sodium carbonate, acetic acid, potassium dihydrogenphosphate, sodium dihydrogenphosphate dihydrate, disodium hydrogenphosphate dodecahydrate, sodium chloride, polysorbate 80, sodium edetate and benzalkonium chloride at the values shown in Table 1.

The figures for each ingredient shown in Table 1 are expressed as % by weight (w/v) and the appearance of each of the preparations are shown as the state before sterilization by filtration based on the following criteria:

<<appearances>> +:cloudy, −:colorless and clear

TABLE 1

|  | Reference Preparation 1 | Reference Preparation 2 | Reference Preparation 3 | Reference Preparation 4 | % by weight (w/v) Reference Preparation 5 |
| --- | --- | --- | --- | --- | --- |
| Boric acid | 1.6 | 1.6 | — | — | — |
| Sodium borate | 0.8 | 0.8 | — | — | — |
| Sodium carbonate | — | — | 0.36 | — | — |
| Acetic acid | — | — | — | 0.035 | — |
| Potassium dihydrogenphosphate | — | — | 0.72 | — | — |
| Sodium dihydrogenphosphate dihydrate | — | — | — | — | 0.31 |
| Disodium hydrogenphosphate dodecahydrate | — | — | — | 2.5 | 0.72 |
| Sodium chloride | — | — | 0.18 | — | 0.59 |
| Polysorbate 80 | 0.1 | — | 0.1 | 0.1 | 0.1 |
| Sodium edetate | 0.01 | — | 0.01 | 0.01 | 0.01 |
| Pranoprofen | 0.1 | 0.1 | 0.1 | 0.1 | 0.1 |
| Benzalkonium chloride | 0.005 | 0.005 | 0.005 | 0.005 | 0.005 |
| Appearances | − | + | − | − | − |
| pH | 7.6 | 7.6 | 7.6 | 7.6 | 7.6 |

As apparent from Table 1, In the preparations containing boric acid, sodium borate and benzalkonium chloride, a change in the composition occurred and cloudiness was observed unless polysorbate 80 and sodium edentate were formulated. In addition, when this cloudy liquid was sterilized by filtration, the content of pranoprofen was decreased.

EXAMPLE

Tromethamine (2 g) was added to sterile purified water (80 ml), and pranoprofen (100 mg) was added thereto while stirring to completely dissolve it. To this was added benzalkonium chloride (5 mg) to dissolve it, an appropriate amount of hydrochloric acid or sodium hydroxide was added to adjust the pH to 7.6, sterile purified water was added to a total volume of 100 ml. The resulting colorless and clear solution was finally sterilized by filtration to obtain a 0.1% pranoprofen ophthalmic solution as preparation 1.

Then, preparations 2 to 9 were prepared according to the similar manner as that described above by fixing the concentrations of pranoprofen and benzalkonium chloride at 0.1% and 0.005%, respectively, and setting the concentrations of tromethamine, HEPES, sodium chloride, polysorbate 80 and sodium edetate at the values shown in Table 2.

The figures for each ingredient in Table 2 are expressed as % by weight (w/v) and the appearance of each of the preparations are shown as the state before sterilization by filtration based on the following criteria:

<<appearances>> +: cloudy, −: colorless and clear

TABLE 2

| | Preparation 1 | Preparation 2 | Preparation 3 | Preparation 4 | Preparation 5 | Preparation 6 | Preparation 7 | Preparation 8 | Preparation 9 |
|---|---|---|---|---|---|---|---|---|---|
| | | | | | | | | | % by weight (w/v) |
| Tromethamine | 2.0 | 2.0 | 2.0 | 2.0 | 2.0 | 2.5 | 0.5 | 1.0 | — |
| HEPES | — | — | — | — | — | — | — | — | 2.0 |
| Sodium chloride | — | — | — | — | — | — | 0.68 | 0.45 | 0.5 |
| Polysorbate 80 | — | — | 0.1 | 0.1 | 0.1 | 0.1 | 0.1 | 0.1 | 0.1 |
| Sodium edetate | — | — | — | — | 0.01 | 0.01 | 0.01 | 0.01 | 0.01 |
| Pranoprofen | 0.1 | 0.1 | 0.1 | 0.1 | 0.1 | 0.1 | 0.1 | 0.1 | 0.1 |
| Benzalkonium chloride | 0.005 | 0.005 | 0.005 | 0.005 | 0.005 | 0.005 | 0.005 | 0.005 | 0.005 |
| Appearances | — | — | — | — | — | — | — | — | — |
| pH | 7.6 | 8.0 | 7.6 | 8.0 | 7.6 | 7.6 | 7.6 | 7.6 | 7.6 |

As apparent from Table 2, in the preparations containing tromethamine and benzalkonium chloride, cloudiness was not recognized and colorless and clear solutions were obtained regardless of inclusion of polysorbate 80 and sodium edetate and, thus, it was found that the present ophthalmic solution does not cause a change in the composition.

Effect of the Invention

Preparation properties test

1) Stability test I (Effect on the remaining rate of pranoprofen)

In order to study the stability of the present ophthalmic solution, the remaining rate of pranoprofen which is an active ingredient was measured.

(Test procedures)

An ophthalmic solution was filled into an eyedropper made of polyethylene, which was stored at a temperature of 40° C. and humidity of 75% for two months, and the amount of pranoprofen in the solution was measured quantitatively by high performance liquid chromatography.

(Results)

Table 3 shows an example of the remaining rates of pranoprofen in preparations (preparation 1, preparation 2, preparation 3 and preparation 4) containing tromethamine and a preparation (reference preparation 1) containing boric acid.

TABLE 3

| | Remaining rate |
|---|---|
| Preparation 1 | 98.6% |
| Preparation 2 | 99.9% |
| Preparation 3 | 98.7% |
| Preparation 4 | 100.2% |
| Reference preparation 1 | 94.9% |

As apparent from Table 3, in the preparations containing tromethamine, the remaining rate was 98% or higher under the aforementioned conditions and no effect on the remaining rate of pranoprofen was recognized.

2) Stability test II (Effect on pH at storage)

In order to study the stability of the present ophthalmic solution, a pH change at storage was measured by the following procedures.

(Test procedures)

An ophthalmic solution was filled into an eyedropper made of polyethylene, which was stored at a temperature of 60° C. for two weeks, and the pH of the solution was measured.

(Results)

Table 4 shows an example of pH changes in the preparations (preparation 1, preparation 2, preparation 3, preparation 4 and preparation 5) containing tromethamine and a preparation (reference preparation 3) containing sodium carbonate and potassium dihydrogenphosphate.

TABLE 4

| | pH Before storage → After storage |
|---|---|
| Preparation 1 | 7.6 → 7.6 |
| Preparation 2 | 8.0 → 8.0 |
| Preparation 3 | 7.6 → 7.6 |
| Preparation 4 | 8.0 → 8.0 |
| Preparation 5 | 7.6 → 7.6 |
| Reference preparation 3 | 7.6 → 9.0 |

As apparent from Table 4, in the preparations containing tromethamine, no pH change was recognized under the aforementioned conditions.

From the results 1) and 2), it was made clear that the present ophthalmic solution has an excellent stability.

3) Eye stimulating test

In order to study the safety of the present ophthalmic solution, the irritating properties in human eyes were measured by the following procedures.

(Test procedures)

The eyes of 5 to 10 healthy male humans were instilled with the present ophthalmic solution, the degree of irritation was evaluated based on the criteria shown in Table 5 and an average of the scores was adopted as an index for a degree of stimulation.

TABLE 5

| Degree of stimulation | Score |
|---|---|
| Sensation of no stimulation | 0 |
| Sensation of weak stimulation | 1 |
| Sensation of stimulation | 2 |
| Sensation of strong stimulation | 3 |

(Results)

Table 6 shows an example of degrees of irritation in the preparations (preparation 1, preparation 2, preparation 3, preparation 5 and preparation 9) containing tromethamine, a preparation (reference preparation 4) containing acetic acid and disodium hydrogenphosphate dodecahydrate, and a preparation (reference preparation 5) containing sodium dihydrogenphosphate dihydrate and disodium hydrogenphosphate dodecahydrate.

TABLE 6

|  | Degree of stimulation |
| --- | --- |
| Preparation 1 | 0.6 |
| Preparation 2 | 0.4 |
| Preparation 3 | 1.0 |
| Preparation 5 | 0.0 |
| Preparation 9 | 0.25 |
| Reference preparation 4 | 1.8 |
| Reference preparation 5 | 1.6 |

As apparent from Table 6, a degree of stimulation was 1 or less and little ocular irritation was recognized in the preparations containing tromethamine or HEPES and, thus, it was made clear that the present ophthalmic solution is an ophthalmic solution having little ocular irritation.

As described above, the present ophthalmic solution is an ophthalmic solution having no change in the composition, an excellent stability and little irritation to eyes and, thus, is useful as an ophthalmic solution containing pranoprofen as an active ingredient.

INDUSTRIAL APPLICABILITY

According to the present invention, there is provided an ophthalmic solution having pranoprofen as an active ingredient, which has no change in the composition, an excellent stability and little irritation to eyes.

What is claimed is:

1. An ophthalmic solution comprising an effective ophthalmic amount of pranoprofen as an active ingredient, an amount of benzalkonium chloride effective as a preservative, and an amount of tromethamine effective to keep the solution stable and clear and lowers eye irritation, said tromethamine being in a concentration of 1 to 2.5% by weight.

2. The ophthalmic solution according to claim 1, wherein the pranoprofen is in a concentration of 0.01 to 0.5% by weight of.

3. The ophthalmic solution according to claim 1, wherein the tromethamine is in a concentration of 2.5% by weight.

4. The ophthalmic solution according to claim 1, wherein the tromethamine is in a concentration 2.0% by weight.

5. The ophthalmic solution according to claim 1, wherein the pranoprofen is in a concentration of 1.0% by weight.

6. The ophthalmic solution according to claim 1, wherein the benzalkonium chloride is in a concentration of 0.002 to 0.01% by weight.

7. The ophthalmic solution according to claim 1, wherein the benzalkonium chloride is in a concentration of 0.005% by weight.

8. The ophthalmic solution according to claim 1, which has a pH of 6.5 to 8.5.

9. The ophthalmic solution according to claim 1, which has a pH of 7.6 to 8.0.

10. A stable and clear ophthalmic solution for decreasing eye irritation comprising 0.01 to 0.5% by weight of pranoprofen, 1 to 2.5% by weight of tromethamine and 0.002 to 0.01% by weight of benzalkonium chloride, and having a pH of 6.5 to 8.5.

11. A stable and clear ophthalmic solution for decreasing eye irritation comprising 0.1% by weight of pranoprofen, 1 to 2.5% by weight of tromethamine and 0.005% by weight of benzalkonium chloride, and having a pH of 7.6 to 8.0.

12. The ophthalmic solution according to claim 1, which further comprises (i) an isotonic agent selected from the group consisting of sodium chloride and glycerin; (ii) a surfactant selected from the group consisting of polyoxyethylene sorbitan monooleate, stearic polyoxyl 40 and polyoxyethylene hydrogenated castor oil; and (iii) a stabilizing agent selected from the group consisting of sodium edetate and sodium citrate.

13. The ophthalmic solution according to claim 1, wherein the pranoprofen is in a concentration of 0.01 to 0.5% by weight and the benzalkonium chloride is in a concentration of 0.002 to 0.01% by weight.

14. The ophthalmic solution according to claim 1, wherein the tromethamine is in a concentration of 1% by weight.

15. The ophthalmic solution according to claim 1, wherein the tromethamine is in a concentration of 2% by weight.

16. The ophthalmic solution according to claim 10, wherein the tromethamine is in a concentration of 1 by weight.

17. The ophthalmic solution according to claim 10, wherein the tromethamine is in a concentration of 2.5% by weight.

18. The ophthalmic solution according to claim 11, wherein the tromethamine is in a concentration of 1 by weight.

19. The ophthalmic solution according to claim 11, wherein the tromethamine is in a concentration of 2.5% by weight.

* * * * *